(12) United States Patent
Mattern et al.

(10) Patent No.: US 7,767,228 B2
(45) Date of Patent: Aug. 3, 2010

(54) PHARMACEUTICAL COMPOSITION FOR ORAL APPLICATION AND METHOD FOR PREPARING THEREOF

(75) Inventors: Claudia Mattern, Stans (CH); Wilfried Pieper, Bergheim (DE)

(73) Assignee: Cum Pharma Consulting Anstalt, Vadux (LI)

( * ) Notice: Subject to any disclaimer, the term of this patent is extended or adjusted under 35 U.S.C. 154(b) by 1763 days.

(21) Appl. No.: 10/794,310

(22) Filed: Mar. 5, 2004

(65) Prior Publication Data

US 2005/0186272 A1 Aug. 25, 2005

(30) Foreign Application Priority Data

Feb. 20, 2004 (EP) .................................. 04003906

(51) Int. Cl.
A61K 9/14 (2006.01)
A61K 9/20 (2006.01)
(52) U.S. Cl. ................... 424/484; 424/464; 424/465
(58) Field of Classification Search ................ 424/484
See application file for complete search history.

(56) References Cited

U.S. PATENT DOCUMENTS

| 1,879,601 | A | | 9/1932 | Chandler et al. | |
|---|---|---|---|---|---|
| 3,264,184 | A | | 8/1966 | Geiger et al. | |
| 3,709,833 | A | * | 1/1973 | Thomas | 502/8 |
| 5,013,716 | A | * | 5/1991 | Cherukuri et al. | 514/23 |
| 5,725,884 | A | * | 3/1998 | Sherwood et al. | 424/489 |
| 5,741,524 | A | * | 4/1998 | Staniforth et al. | 424/489 |
| 5,827,497 | A | * | 10/1998 | Camilleri et al. | 424/1.37 |
| 6,004,582 | A | * | 12/1999 | Faour et al. | 424/473 |
| 6,110,205 | A | * | 8/2000 | Nies | 623/11.11 |
| 6,352,721 | B1 | * | 3/2002 | Faour | 424/473 |
| 6,491,949 | B2 | * | 12/2002 | Faour et al. | 424/473 |
| 6,555,139 | B2 | * | 4/2003 | Sharma | 424/489 |
| 2003/0064029 | A1 | * | 4/2003 | Tarara et al. | 424/45 |
| 2005/0014060 | A1 | * | 1/2005 | Suzuki | 429/41 |

FOREIGN PATENT DOCUMENTS

| EP | 1362583 | 11/2003 |
|---|---|---|
| SU | 1465052 | 3/1989 |

OTHER PUBLICATIONS

Answers.com;(Dictionary) activated charcoal, Sci-Tech Encyclopedia (2007), printed pp. 1-7.*
Bet (B.E.T.) surface area summary [online], retrieved: Jan. 22, 2008, retrieved from http://www.clearsci.com/BET.htm.*
West, L., Pediatric Nursing; Innovative approaches to the administration of activated charcoal in pediatric toxic ingestions, 1997, printed pp. 1-7, especially pp. 2-5.*
Ilkhanipour et al., Activated charcoal surface area and its role in multiple-dose charcoal therapy Am J Emerg Med. Nov. 1993;11(6):583-5.*

* cited by examiner

*Primary Examiner*—Sreeni Padmanabhan
*Assistant Examiner*—Timothy E Betton
(74) *Attorney, Agent, or Firm*—Frommer Lawrence & Haug LLP; Sandra Kuzmich; Heather J. DiPietrantonio

(57) ABSTRACT

The present invention relates to a pharmaceutical composition for oral application comprising: i) an anthelmintic agent; ii) a first excipient having a porous structure with an inner surface of about 500 to 1500 $m^2/g$ and a surface area according to BET of up to about 5000 $m^2/g$; as well as to a method of preparing such a composition.

9 Claims, 1 Drawing Sheet

PHARMACEUTICAL COMPOSITION FOR ORAL APPLICATION AND METHOD FOR PREPARING THEREOF

BACKGROUND OF THE INVENTION

1. Field of the Invention

Figure 1:
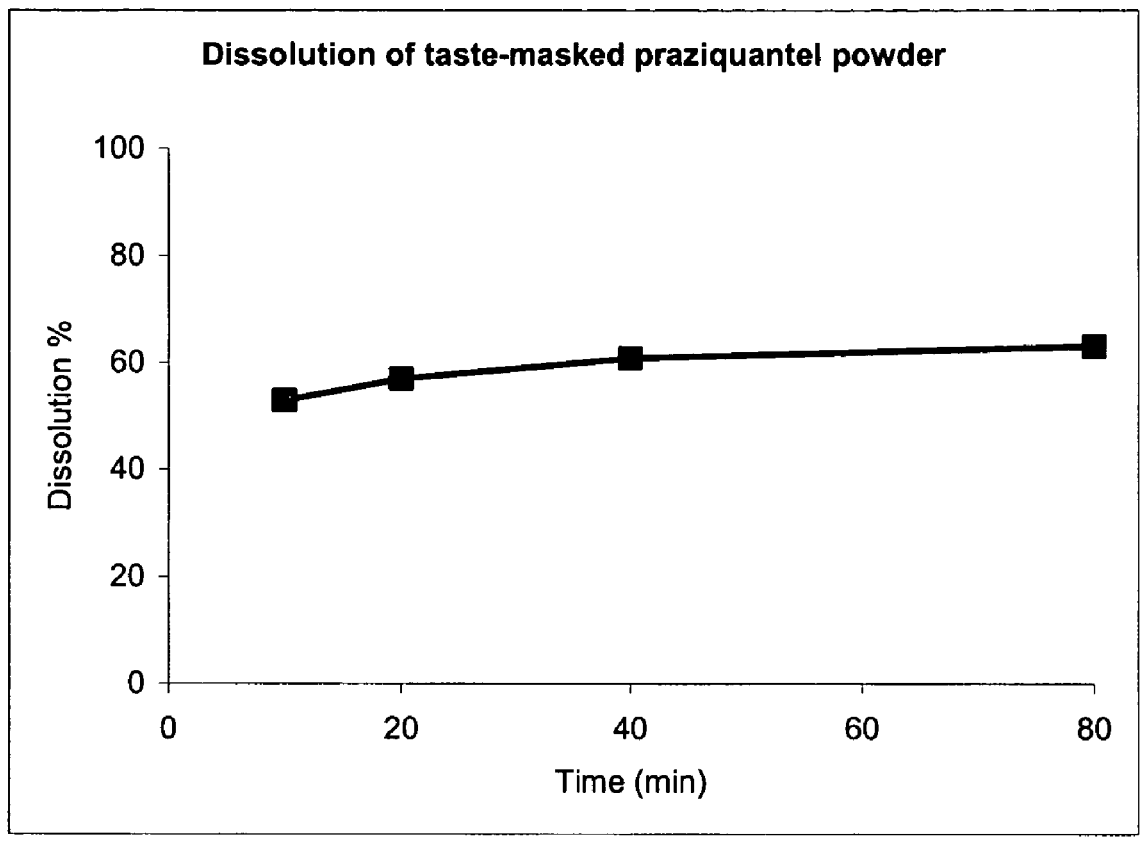

The invention relates to a pharmaceutical composition for oral application and to a method of preparing thereof.

2. Description of the Related Art

Pharmaceutical drugs often have certain desirable properties but an undesirable smell and/or taste. These properties have a great impact on patient compliance and marketing of the pharmaceutical product. This is especially true for animals having an extremely well-developed sense of taste and smell.

In general drug delivery systems for taste masking can be achieved by either chemically or physically modifying a drug powder. The latter option is more interesting since toxicological investigations of the new compound can be avoided.

In general physical taste masking technologies rely on preventing interaction between the drug molecule and the oral mucosal surface and various approaches and several manufacturing processes for masking the unpleasant taste of drugs as solid dosage forms have been proposed. These include barrier methods (embedding, coating, encapsulation), use of flavours and sweeteners and complexation and adsorption approaches. Thus taste masked powders are formed by methods known of the art such as spray drying, granulation and coacervation. A review is given, for example, in SUN et al. (American Pharmaceutical Review, 16-28, 1999).

For complexation, adsorption and inclusion of bad-tasting drugs ion-exchange resins, ionic polymers (acrylic acid-/cellulose-derivates, chitosan), cyclodextrins and other additives such as phospholipids or tannic acid have been used.

Taste-masking of ionic drugs can be achieved using materials containing basic or acidic groups that interact with the ionisable molecule thus creating insoluble salts. Since bitter drugs in non-dissolved state have no taste the idea is that the drug is not dissolved, i.e. released, during passage through the mouth. Nature and extend of the interaction between the drug and the additive depend on factors such as pK of the drug and the additive, ionic strength, pH of the fluid, solubility of the drug and chemical structure of the additive.

Thus Prabhu, N. (Indian Journal of Pharmaceutical Sciences, May-June 2002) described taste masking of clarithromycin by complexation with tannic acid.

U.S. Pat. No. 5,219,563 (Douglas, S. J., 1990) and U.S. Pat. No. 3,594,470 (Borodkin, S. and Sundberg, D. P., 1971) provide methods of taste-masking by loading the anionic drug onto a methacrylic acid/divinylbenzene copolymer (Amberlite®).

U.S. Pat. No. 3,974,272 (Polli, G. P. and Shoop, C. E., 1976) provide a method for a palatable cholestyramine coacervate by loading a cationic drug onto a styrene/divinylbenzene copolymer (Duolite®).

U.S. Pat. No. 5,560,921 (Damani, N. C. and Viehues, R., 1995) and U.S. Pat. No. 4,971,791 (Tsau, J. H. and Damani, N. C, 1990) provide a method of taste-masking by complexing the drug with a polymethacrylate polymer.

More complicated is the taste-masking of neutral drugs by complexation/adsorption as can be deduced form the number patent applications.

Carbohydrates e.g. can entrap hydrophobic/lipophilic drugs. Most commonly taste-masking is achieved by inclusion of the bitter drug in cyclodextrin cavities, where the binding of the bitter guest molecule within the host cyclodextrin is not fixed or permanent but a dynamic equilibrium (Szejtli, J., Medicinal Research Review, 14(3): 353-386, 1994).

U.S. Pat. No. 5,681,577 (Lech, S., Schobel, A. M. and Denick, J., 1995) provides a different approach and a method of taste-masking by adsorbing the drug (pseudoephedrine, dextromethorphan, diphenhydramine) to silicon dioxide, U.S. Pat. No. 4,647,459 (Peters, D., Denick, J. and Talwar, A. K.) uses magnesium trisilicate for adsorption.

Charcoal is well-know and commonly used to prevent absorption of drugs from the gastrointestinal tract in case of intoxication by adsorbing them. Charcoal is also used for blood purification in hemoperfusion. A less common effect used in medicine is the adsorption effect of charcoal on *Escherichia coli* or aflatoxin. The indications mentioned above are only dealing with the adsorption effect of charcoal.

Some investigators however have taken into consideration that, as in cyclodextrins, adsorption is not a one-way process but there is also some desorption of a drug from charcoal. They are using charcoal as excipient for sustaining the release of a drug in the gastrointestinal tract (e.g. Roivas, L. et al., Methods Find Exp Clin Pharmacol, 16(2):125-32, 1994). However, sustained release of a drug from an excipient does not automatically lead to the assumption that the excipient may be advantageously used for taste masking of a drug.

Up to now taste-masked particles produced by the methods mentioned above often suffer from problems such as:

- Only drugs can be used that either have cationic functionality (e.g. —COOH or Na/K salts) or anionic functionality (e.g. —NH$_2$, HCl salts etc.);
- The taste barrier is physically damaged during further processing of the drug to the finished product, e.g. by the tabletting process;
- The barrier is physically damaged during ingestion by chewing on it. This happens when the particles are too big because only particles smaller than 50 μm (the distance between taste buds in the mouth) don't give a sandy mouth feel. This demand is challenging because smaller particles have a larger surface area-to-volume ratio and dissolve more rapidly in the mouth than larger particles;
- Maintaing acceptable sensory attributes cannot be achieved while achieving acceptable bioavailability. This is especially problematic in the case of low-soluble drugs such as those of BCS system class II and IV.
- One possible problem is that the complexation force is too strong leading to a sustained release of the drug.
- Another possible problem is that some pharmaceutical compositions are using the concept that, at the pH in the mouth (approximetly 5.9-7.8), the drug remains insoluble. However this is also the pH which can be found in the intestinal tract and where the drug has to be dissolved because absorption takes place;
- Commonly used complexing or coating agents are soluble or somewhat permeable at the pH of the saliva. E.g. Eudragit L (methacrylic acid copolymer A) is soluble from pH 5.5, Eudragit S (methacrylic acid copolymer) is soluble from pH 7;
- The threshold concentration for bitter taste of the drug is very low;
- The drug to be coated has an unfavourable crystal form, e.g. in the case of praziquantel a needle;
- The technologies involved are rather sophisticted i.e. solvents are used or risky technologies such as nano particle systems, several steps are necessary during production and/or special equipment;

Moreover, S. T. Hong et al., Parasitol Res., Oct. 1, 2003; 91(4): 316-20 further describes that it is desirable to apply an anthelmintic drug in a sustained release form using hydroxypropylmethylcellulose as carrier. Not only because plasma concentrations are short due to their rapid absorption and secretion after ingestion but also because some of them are mainly acting by direct contact with the parasite in the gastrointestinal tract making it desirable that the dose remains in the gastrointestinal tract for a longer time. As starch and cellulose are soluble and swellable, respectively, in water i.e. in the spittle, taste-masking of the drug is not at all sufficient.

SUMMARY OF INVENTION

Therefore, it is an object of the present invention to overcome the drawbacks of the prior art, especially to provide a pharmaceutical composition comprising an anthelmintic agent, wherein the pharmaceutical composition shows improved taste-masking and sustained release.

It is another object of the invention to provide a method for preparing such a pharmaceutical composition.

The object is achieved by a pharmaceutical composition for oral application comprising an anthelmintic agent and a first excipient having a porous structure with an inner surface of about 500 to about 1.500 m$^2$/g and a surface area according to BET of up to about 5.000 m$^2$/g.

Preferably, the agent is a non-charged agent.

Still preferably, the agent is selected from the group consisting of macrolides, benzimidazoles, isoquinolones, pyrantel or mixtures thereof.

More preferably, the agent is ivermection, febantel, fenbendazole, praziquantel, epsiprantel or mixtures thereof. Most preferably, the agent is praziquantel or epsiprantel.

In one embodiment, the excipient is charcoal.

The Brumauer, Emmett, Teller (BET) method is a commonly used well known method for determining the total surface area of a give material. Gas sorption (both adsorption and desorption) at the clean surface of dry solid powders is the most popular method for determining the surface area of these powders as well as the pore size distribution of porous materials. In a gas sorption experiment, the material is heated and degassed by vacuum force or inert gas purging to remove adsorbed foreign molecules. Controlled doses of an inert gas, such as nitrogen, krypton, or argon, are introduced and the gas is adsorbed, or alternatively, withdrawn and desorbed. The sample material is placed in a vacuum chamber at a constant and very low temperature, usually at the temperature of liquid nitrogen (−195.6° C.), and subjected to a wide range of pressures, to generate adsorption and desorption isotherms. The amounts of gas molecules adsorbed or desorbed are determined by the pressure variations due to the adsorption or desorption of the gas molecules by the material (the adsorbent). Various amounts of gas molecules will be adsorbed or desorbed at different doses of the gas (the adsorbate). Knowing the area occupied by one adsorbate molecule, σ (for example, σ=16.2 Å$^2$ for nitrogen), and using an adsorption model, the total surface area of the material can be determined. The most well known and widely used is the BET equation for multilayer adsorption[1]:

$$\frac{P}{n(P_0 - P)} = \frac{1}{cn_m} + \frac{c-1}{cn_m} \frac{P}{P_0}. \quad (1)$$

In Eq. 1, P, P$_o$, c, n, n$_m$ are the adsorption pressure, the saturation vapor pressure, a constant, the amount adsorbed (moles per gram of adsorbent) at the relative pressure P/P$_o$, and the monolayer capacity (moles of molecules needed to make a monolayer coverage on the surface of one gram of adsorbent), respectively. Through the slope and intercept of a plot of P/[n(P$_o$−P)] against (P/P$_o$), n$_m$ can be resolved. The specific surface area, S, can then be derived:

$$S = N_A n_m \sigma. \quad (2)$$

In Eq. 2, N$_A$ is Avogadro's number. The specific surface area that can be determined by gas sorption ranges from 0.01 to over 2000 m$^2$/g. Determination of pore size and pore size distribution of porous materials can be made from the adsorption/desorption isotherm using an assessment model, suitable for the shape and structure of the pores. The range of pore sizes that can be measured using gas sorption is from a few Angstroms up to about half a micron.

Most preferably, the invention is characterized in that the excipient is activated charcoal.

A further embodiment is characterized in that the charcoal has a surface area according to BET of about 1400 to about 2100 m$^2$/g, preferably about 1700 m$^2$/g.

Preferably, the excipient is present in the composition in an amount of from about 30 to about 98% by weight, more preferably about 50 to about 90% by weight and most preferably at about 70% by weight.

Preferably, the excipient having the agent adsorbed has a particle size of less than 50 μm.

A further embodiment is characterized in that the agent is preferably adsorbed to the inner pores of the excipient.

Preferably, the excipient is muco-adhesive in the gastrointestinal tract and/or taste-masking.

Preferably, the composition comprises a second excipient being adsorbed to the core of the first excipient.

In a preferred embodiment, the pharmaceutical composition is coated or encapsulated.

Preferably, the pharmaceutical composition further comprises adjuvants, flavours, diluents or the like.

A further object of the invention is achieved by a method of preparing a pharmaceutical composition according to the invention, comprising the step of mixing the agent and the excipient in a dry state.

A preferred embodiment is characterized in that the mixing is carried out under agitation with high speed.

Finally, it is preferred that in a preceding step a second excipient is first adsorbed to the core of the first excipient.

Surprisingly it was found that with the present invention a taste-masked, preferably mucoadhesive, pharmaceutical composition of small particle size for additional pH-independent sustained release of the active ingredient in the gastrointestinal tract and its method of preparation using a very simple, solvent-free procedure is provided.

By the procedure described the anthelmintic agent is adsorbed to the inner surface of an excipient having a porous structure with particular surface area providing an efficient, taste- and odour-masking effect as well as sustained release profil. This excipient is preferably activated charcoal.

The resulting taste-masked powder can be coated and/or further processed with flavours and other pharmaceutical excipients to form a suitable product.

Surprisingly it was found by the applicant that for the adsorption of a hydrophobic/lipophilic compound not only a large surface of a suitable adsorbent particle (excipient) is of great importance but especially a specific porous structure. Especially taste-masking is clearly improved when the bitter drug is not adsorbed on the outer surface of the excipient but is entrapped in the pores. Using charcoal as excipient, no desorption of the anthelminitic agent is detectable in the mouth.

The term "excipient having a porous structure" shall mean a porous powder with a high inner surface able to adsorb compounds to this surface.

Thus the excipient is a highly porous substance providing surface forces to the agent. Result of the surface interaction is the accumulation of the agent at the surface region of the excipient.

As excipient (adsorbent) can be used excipients having pores from nature such as charcoal (inner surface about 500-1500 $m^2/g$, BET up to 5000 $m^2/g$) or excipients where pores are introduced into the particles by special treatment such as starch (e.g. potato starch special quality/Nichiden Chemical) or silicates (e.g. silica gel). Especially suitable in this sense is activated charcoal and therefore is most preferred in the current application. In this regard, NORIT A SUPRA® is one preferred activated charcoal having a BET surface area of about 1700 to about 2100 $m^2/g$ with a methylene blue adsorption of about 35 to about 45 g/100 g charcoal and a phenazone adsorption of about 45 to about 55 g/100 g charcoal.

Up to now charcoal has never been considered as having taste-masking properties in pharmaceutical drugs. Surprisingly it was found by the applicant that by embedding of a non-charged active ingredient, namely an anthelmintic agent, into charcoal the taste of the agent can extremely be masked efficiently. This is mainly caused by the fact that the agent is adsorbed into the inner surface (pores).

The excipient for the inventive pharmaceutical composition has also muco-adhesive properties enabling the agent to remain in the gastrointestinal tract for a prolonged time and providing sustained adsorption of the active ingredient. Such an excipient may therefore be used to prolong the systemic adsorption of anthelmintic drugs and/or to make it available at the local site of action, the intestinal surface.

The pharmaceutical composition of the invention may be prepared in a fast and cost effective manner. Preferably, the hydrophobic/lipophilic agent is adsorbed to the core or to a core-mixture of excipient(s). I.e. either the agent is adsorbed directly to the core or, in a preceding step, another excipient is first adsorbed to the core to close the finest pores thus improving the release of the agent. A suitable excipient for the preceding step is one of small particle size such as colloidal silicon dioxide.

The adsorption method is high-speed mixing of agent and excipient in dry state or dispersing the mixture in water or a solvent where the agent is dissolved. The latter methods are followed by evaporation of the solvent.

Especially preferred however is mechanical impact blending of the agent mixture (hybridization) because of the simple, fast procedure and the waive of any further additive such as binder or solvent.

The hybridization technique has mainly been developed by the Japanese company NARA (NARA Machinery Co. Ltd., Tokyo) and is described in EP 0 224 659 A2 "Method of improving quality of surface of solid particles and apparatus thereof". Briefly, a powder mixture from the powder inlet is carried on an air stream generated by blades rotating at high speed, and circulates in the machine through a cycling tube. In the machine, the excipient collide with the agent, the blade, and the inner surface of the machine.

By this method the active ingredient is converted directly, by a one-step-procedure, into a very uniform product composed of particles of not more than 50 μm.

If needed the dissolution kinetics of the so-processed pharmaceutical composition can be modified by conventional coating or embedding methods.

DETAILED DESCRIPTION OF THE INVENTION

The invention is now further illustrated by way of example with reference to the accompanying drawing, wherein the figure shows the dependency of dissolution on time for a taste-masked and sustained release praziquantel powder.

The present invention is illustrated using the active ingredient praziquantel, a hydrophobic/lipophilic anthelmitic drug with short elimination half-time having a low solubility in water and being extremely bitter in taste. An invention pharmaceutical composition can be preferably utilized in the treatment of animals with an anthelminitic agent.

A good taste-masking and sustained release of praziquantel was achieved by the following mixture:

| Compound | Amount (w/w) |
| --- | --- |
| Praziquantel | 20% |
| Colloidal silicon dioxide (Aerosil 200) | 10% |
| Activated charcoal (Norit A Supra) | 70% |

The corresponding amount of charcoal and Aerosil are mixed (40-300 g) and introduced into a NARA Hybridization System, NHS Type 1. The mixture is processed for 3 min at 6000 rpm. To this pre-mixture the active ingredient praziquantel was added and the finished mixture was again processed for 3 min at 6000 rpm.

Several factors can influence dissolution profiles of drug delivery systems such as pH, thickness and sort of coating or surface wettability. In the case of praziquantel the delay in drug release needs to be long enough to pass the oral cavity, followed by a suitable (fast or sustained) release in the gastrointestinal tract.

Praziquantel has a very low solubility in water and the dissolution according to USP has to be "not less than 75% after 60 minutes". Under conditions as described in USP for praziquantel tablets the release of praziquantel from the powder according to the invention is around 50% after 10 minutes continued by a slow release reaching about 65% after 80 minutes (see figure below).

It is surprising that the release at the site of action is fast although the taste of the adsorption complex in the mouth remains perfect. It must be emphasized that the threshold concentration for bitter taste of praziquantel is very low.

The release in the gastrointestinal tract is adapted to the indication because of the presence of worms in the stomach, not only in the intestine; further, although up to now not realized in dosage forms a prolonged release of praziquantel is desirable (e.g. as explained recently by Hong S. T., supra).

It can be concluded that the pharmaceutical composition for oral application of this invention is different from conventional formulations for taste-masking and/or mucoadhesive action because of the excipients used and the extreme ease and speed of its production.

Further advantages are that the dissolution of the tasteless complex is not pH-dependent, that its particle size is within the range of micronized powders, that there is no artificial smell of excipients as in polymers such as methacrylates (especially useful in veterinary medicine) and that the taste barrier cannot physically be damaged during a tabletting process.

The features disclosed in the foregoing description, in the claims and/or in the accompanying drawings may, both separately and in any combination thereof, be material for realizing the invention in diverse forms thereof.

The invention claimed is:

1. A pharmaceutical composition for oral application comprising:
   (a) an anthelmintic agent;
   (b) a first taste-masking excipient having a porous structure with an inner surface of about 1400 to about 2100 m2/g wherein absorption of the anthelmintic agent occurs and a surface area according to Brunauer Emmett Teller method of up to about 5000 m2/g; and
   (c) a second excipient adsorbed to the core of the first excipient,
   wherein the anthelmintic agent is selected from the group consisting of ivermection, febantel, fenbendazol, praziquantel, epsiprantel and mixtures thereof,
   wherein the first excipient is charcoal or activated charcoal present in an amount of about 50% to about 70% by weight and having the agent adsorbed has a particle size of less than 50 µm, and
   wherein the second excipient is colloidal silicon dioxide.

2. The pharmaceutical composition according to claim 1, wherein the agent is adsorbed to the inner pores of the excipient.

3. The pharmaceutical composition according to claim 1, wherein the first excipient is mucoadhesive in the gastrointestinal tract.

4. The pharmaceutical composition according to claim 1, wherein the pharmaceutical composition is coated or encapsulated.

5. The pharmaceutical composition according to claim 1, wherein the pharmaceutical composition further comprises adjuvants, flavours, and/or diluents.

6. A method of preparing a pharmaceutical composition according to claim 1, comprising the step of mixing the agent and the first and or second excipient in a dry state,
   wherein the method of preparation is solvent-free.

7. The method according to claim 6, wherein the mixing is carried out under agitation with high speed.

8. The method according to claim 6, wherein the second excipient is first adsorbed to the core of the first excipient prior to the mixing step.

9. The pharmaceutical composition according to claim 1 wherein the charcoal has a surface area according to the Brunauer Emmett Teller method of 1700 m2/g.

* * * * *

UNITED STATES PATENT AND TRADEMARK OFFICE
CERTIFICATE OF CORRECTION

PATENT NO. : 7,767,228 B2 Page 1 of 1
APPLICATION NO. : 10/794310
DATED : August 3, 2010
INVENTOR(S) : Claudia Mattern et al.

It is certified that error appears in the above-identified patent and that said Letters Patent is hereby corrected as shown below:

In the claims:

Column 7, Claim 1, line 24, replace:

"weight and having the agent adsorbed has a particle size" with
-- weight and the agent adsorbed has a particle size --

Signed and Sealed this

Twenty-first Day of December, 2010

David J. Kappos
*Director of the United States Patent and Trademark Office*